United States Patent [19]
Short et al.

[11] 4,005,705
[45] * Feb. 1, 1977

[54] SPLINTS

[75] Inventors: Douglas Paviour Short; Donald James Gillon; Henry Britton Coates Milsom, all of Tauranga, New Zealand

[73] Assignee: Fisher & Paykel Limited, Auckland, New Zealand

[ * ] Notice: The portion of the term of this patent subsequent to Mar. 1, 1992, has been disclaimed.

[22] Filed: Sept. 10, 1975

[21] Appl. No.: 611,890

Related U.S. Application Data

[63] Continuation of Ser. No. 67,958, Aug. 28, 1970, abandoned.

[30] Foreign Application Priority Data

Aug. 29, 1969 New Zealand ............... 157633

[52] U.S. Cl. .......................................... 128/87 R
[51] Int. Cl.² ...................................... A61F 5/04
[58] Field of Search ............. 128/87 R, 89 R, 83, 128/84, DIG. 15

[56] References Cited
UNITED STATES PATENTS

| | | | |
|---|---|---|---|
| 2,785,672 | 3/1957 | Napoli | 128/87 |
| 3,232,289 | 2/1966 | Zimmerman | 128/DIG. 15 |
| 3,454,002 | 7/1969 | Westlake et al. | 128/87 R |
| 3,528,412 | 9/1970 | McDavid | 128/89 X |
| 3,624,745 | 11/1971 | Bowers | 128/87 |

FOREIGN PATENTS OR APPLICATIONS

| | | | |
|---|---|---|---|
| 12,664 | 9/1915 | United Kingdom | 128/87 R |
| 451,206 | 7/1936 | United Kingdom | 128/87 R |

OTHER PUBLICATIONS

"Emergency Transportation Set" DePuy Fracture Appliance Catalogue, p. 105, May 1966.

*Primary Examiner*—John D. Yasko
*Attorney, Agent, or Firm*—Holman & Stern

[57] ABSTRACT

A Thomas splint in which extendable leg members are pivotally associated with a malleable split ring to enable the splint to be substantially universal for use on either right or left legs and on different sized patients.

2 Claims, 4 Drawing Figures

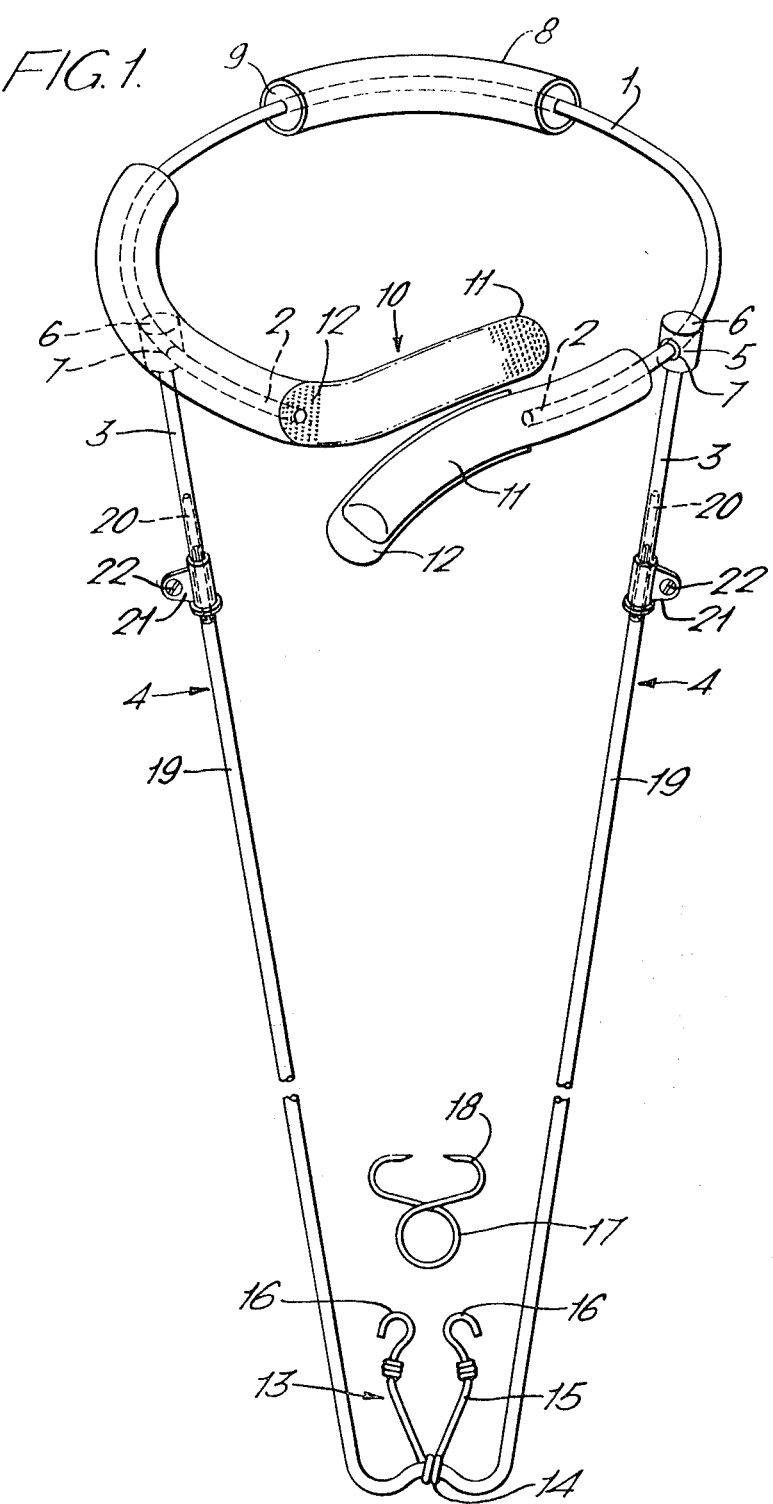

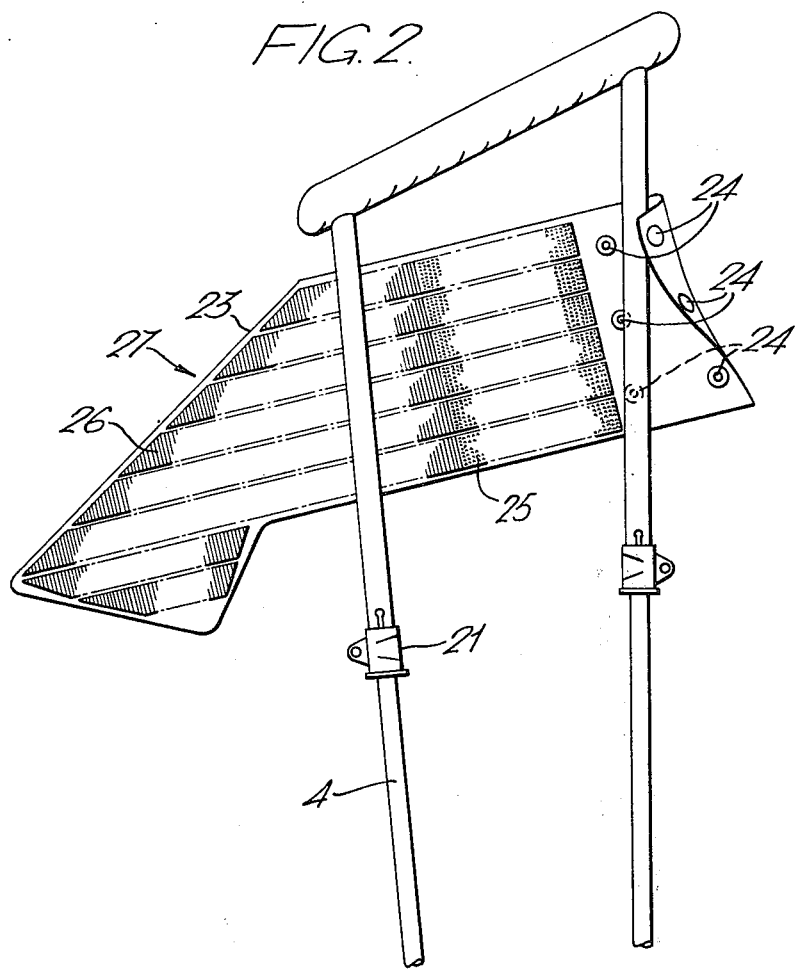
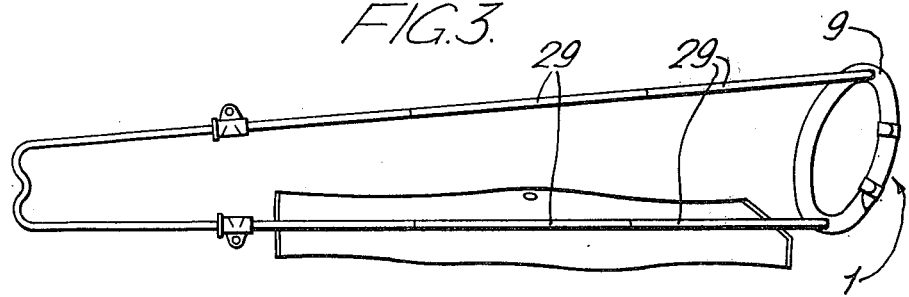

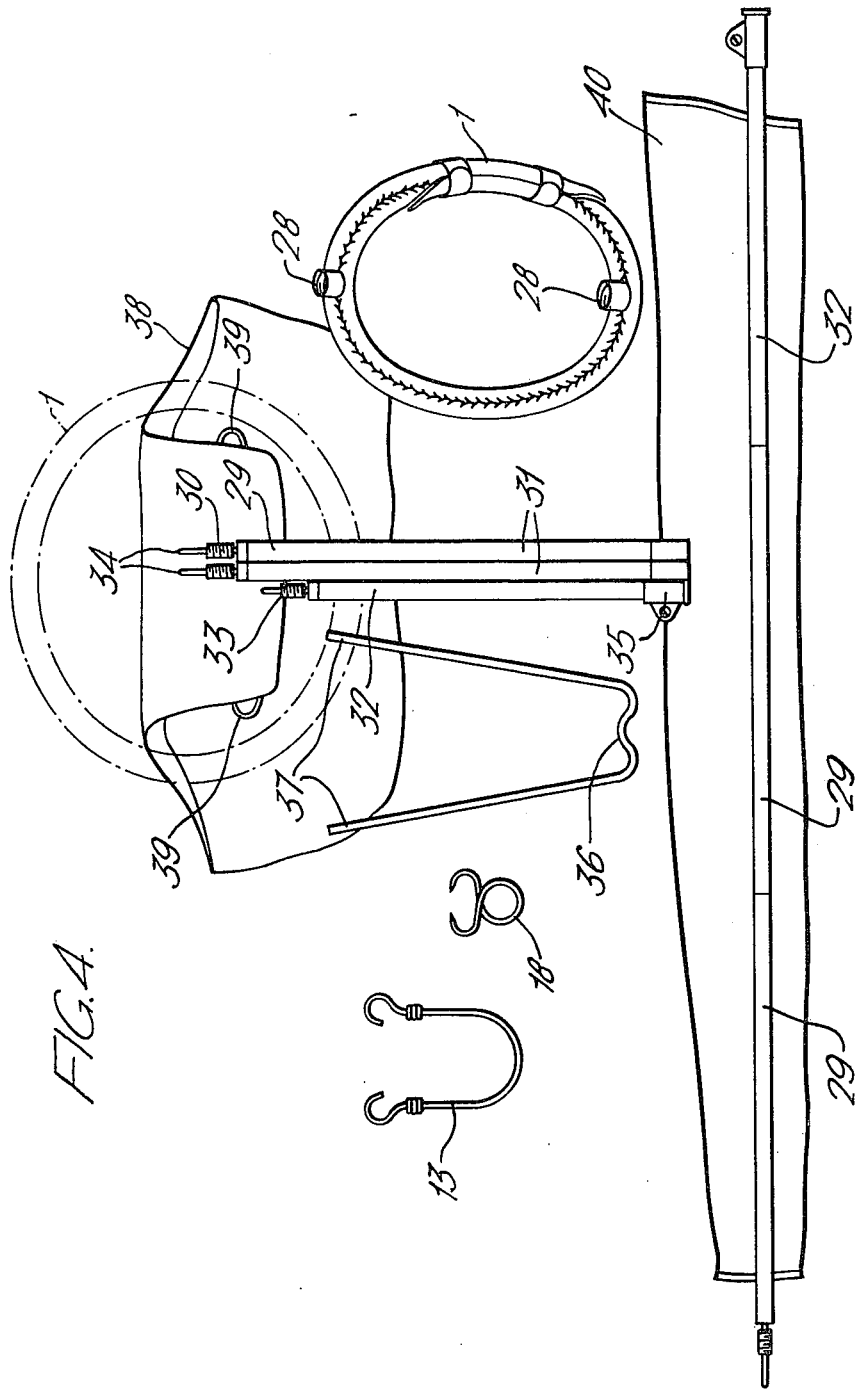

SPLINTS

This is a continuation of application Ser. No. 67,958 filed Aug. 28, 1970 now abandoned.

BACKGROUND OF THE INVENTION

The invention relates to splints.

The effectiveness of the Thomas splint with fixed traction as a first aid measure in fractures of the femur, is proven by its persistence as an item of standard equipment for more than half a century. The Thomas splint, when properly applied, provides a reliable and most useful means of reducing the pain and distress of transport, the extent of shock, the likelihood of soft tissue damage, and the incidence of fat embolism. However, despite the proven effectiveness of the splint, its safe and proper application envisages many difficulties to which a multitude of modifications bears eloquent witness. One of the major disadvantages is, of course, that it is necessary to find Thomas splints which will fit the limb of a particular human being in that, at present, the splints being kept within rigid ring sizes, it is necessary to provide right or left siding; the length must be variable; and it is necessary to provide varying obliquity of the ring. With the fixed sizes as at present provided this, in effect means, for each patient, a new Thomas splint must be made or, at best, a close fit utilized (when found) with its attendant disadvantages.

OBJECT AND SUMMARY OF THE INVENTION

It is, therefore, an object of the present invention to provide a splint which will obviate or minimize the foregoing disadvantages in a simple yet effective manner, or which will at least provide the public with a useful choice.

Accordingly, in one aspect, the invention consists in a splint comprising a foot member, a ring member and a pair of leg members positioned on said ring members by positioning means, adjustable in length and engageable with said foot member, said positioning means, in use, restraining movement of said leg members around the periphery of said ring members, but allowing pivoting relative to the plane of the ring member, the construction and arrangement permitting adjustment of the length of the leg members, and adjustment of the obliquity of the ring member relative to the ring member to assist in adapting the splint to a patient.

Two forms of the invention will now be described, one preferred for use in routine hospital treatment of fracture of the femur, and the second as a rescue splint for first aid treatment of the same in which,

BRIEF DESCRIPTION OF THE DRAWINGS

FIG. 1 is a perspective view of a splint according to the invention, for routine use in hospitals, FIG. 2 is a further perspective view in part of a splint showing one of a preferred form of sling for use with the splint of FIG. 1, FIG. 3 is a perspective view of an assembled rescue splint according to the invention, and FIG. 4 is a perspective view of a rescue pack including the members of the splint which can be fitted in the pack, with one of the leg members being shown partly assembled.

DETAILED DESCRIPTION OF THE INVENTION

Referring to the drawings, a splint according to the invention designed to replace the Thomas hip splint for definitive treatment of a fracture of the femur in hospitals, is constructed as follows:

A ring 1 is made of a malleable material which, for example, comprises an annealed bright steel, the malleability being relative, in other words, by applying an appreciable force to the ring, it may be deformed, but ordinary forces met with during use on a patient, will not deform the ring. The ring is discontinuous, there being a gap between ends 2 of the ring.

Tubular portions 3 of leg members generally referenced 4 are positioned on the ring by positioning means comprising a transverse aperture 5 in a fitting 6 at one end of the tubular portion 3, the aperture 5 fitting over the ring 1, and being positioned on the ring by circumferential enlargements 7, and disposed one on either side of the member 6. This enables the tubular members 3 to pivot using a part of the ring as an axis, but prevents the tubular members 3 from being moved circumferentially of the ring. For the patient's comfort, the ring and part of the members 6, are covered with a flexibly resilient material such as one inch outside diameter "Rubazote" tubing 8 with a bore suitable to the size of the ring wire, for example, a quarter of an inch diameter, and covering the tubing 8, is a soft leather or other outer covering 9, sewn or otherwise fixed over the tubing 8. In a discontinuity or gap 10 between the ends 2 of the ring 1, the tubing 8 is divided into semi circular portions 11, and diametral surfaces 12 of these portions are faced with the complementary parts of a fastening material such as "Velcro" material.

A foot member 13, is provided having a form something like an extended W, with central portion 14 providing a notch or area around which an elastic cord 15 having hooks 16 may be wrapped, the hooks being connected to the patient's leg to apply traction thereto either by being applied to a lock 17 of the spring or Millbank 18 applied to a boot on the patient's foot which is only used for first aid treatment or rescue work and will be referred to again later, or more usually for hospital treatment, to a loop of sticking plaster or other adhesive material such as elastoplast, applied to the skin of the patient in the known way. The member 13 is integral with further parts 19 of the leg members, the parts 19 and foot member being made of rod and upper ends 20 of the parts 19 fitting in the tubular member 3, and being fixed therein by compression clamps 21 having locking means comprising an Allen cap screw slotted nut and bolt wing nut and bolt combination as desired. By this arrangement, the length of the leg members may be adjusted so that the obliquity of the ring relative to the leg members can be adjusted, and the length of the leg members can be adjusted to the length of leg of a patient.

Referring to FIG. 2, slings are provided detachable from the leg members to support the leg and, for example, one of which is shown in FIG. 2. Each sling comprises a textile material backing 23 fixed to one of the leg members by a loop and press stud fasteners 24, and having complementary parts 25 and 26 of a fastener such as a "velcro" fastening material, suitably disposed over most of the surface of the backing material 23. It will be understood that by folding portion 27 of the part 25 over a leg member 4, and sticking the complementary part 26 of the "Velcro" fastener to the portion 27 thereof, a readily adjustable sling is provided.

The foregoing construction is particularly suited, as stated, for definitive treatment in hospitals. However, we have also found that it would be desirable if a more compact portable kit could be provided to enable the invention to be used in the field for first aid treatment. Accordingly, referring to FIGS. 3 and 4, the modifications necessary to enable such equipment to be provided are as follows:

The ring 1 with the tubing and leather coverings 8 and 9, are constructed as above described. The leg members differ, however, in that pivotal attachments 28 are fixed to the ring 1 in a similar manner to that in which the tubular members 3 are fixed as above described, but the members 28 are provided with a female screw thread into which a section 29 of a leg member may be fixed with a male threaded part 30 thereof engaging the female threaded part of the member 28. For each leg member, two sections 29 are provided, assembled end to end, with ends 31 having a female thread therein, corresponding to the female thread in the member 28. A third section 32 is provided for each leg, one end having a male thread 33 and pin 34, the pins 34 being of about core diameter of the male thread 33, and being provided for ease of insertion of the leg members, for example with these pins, such leg members may be assembled in the dark by unskilled personnel. The opposite end of the member 32, has a compression clamp 35 corresponding to the compression clamp 21 in the construction shown in FIGS. 1 and 2. However, this compression clamp is, preferably, fastened with a wing nut and bolt only so that no tools are necessary for joining. A foot member 36 corresponds to the foot member 13, and extends as parts 37 of the leg members, and the free ends of the parts 37 extend into the tubular members 32, and are fixed therein by the compression clamps 35. In this way, the same resultant flexibility and adjustment of size and obliquity of the ring is obtained as with the device shown in FIGS. 1 and 2.

However, with this construction, it is a particular feature that the splint may be disassembled and packed in a bag 38 with the members 28 extending through holes 39 with the ring 1 taking up the disposition as shown by dot-dash lines in FIG. 4, the leg members 29 and 32 and the foot and leg members 36 and 37 being packed in the bag, after which the cover of the bag may be tied. In addition, a stocking form sling 40 is provided which may be assembled over the assembled leg members preparatory to fitting the splint to a patient. Bandages and the Millbank Clip 18 and elastic foot flexible member 15 are also included in the carrying bag 38.

The use of the construction will be clear. By manipulation of the ring 1, the ring may be placed over a patient's leg near its final position, with the patient's leg passing through the opening or discontinuity 10, the ends 11 being suitably separated to permit this. The ring is then manipulated to its final disposition, and the surfaces 12 contacted with each other. By adjusting the length of the leg members, using the compression fittings and sliding the portion 20 in or out of the tubular member 3 in the case of the hospital member, or by sliding the members 37 in and out of the members 32, such length adjustment is possible. Of course, the obliquity of the ring relative to the leg members is effected in the same manner. By securing the locking clamps, the individual setting of the splint is locked and maintained rigidly throughout either first aid or definitive treatment of the fractured femur. In the splint devised for definitive treatment, adjustment of the slings shown in FIG. 2 is readily accomplished with speed and comfort to both patient and operator and, in this particular system, slipping of the slings and painful pricking of the operator's fingers through the use of safety pins as at present used, have been eliminated.

The rescue splint has been evolved for the purposes of rescue or military use, where lightness, ease of stowage, compactness and simplicity of application, and has been found most effective. The single stocking type of sling 40 has been developed for speed and simplicity of application, this being slid over the side members from the distal end of the assembled rescue splint, and can be reversed to allow for different sides thereof to be used.

Since the splint is adjustable for length, in both cases traction can be very quickly applied under rescue circumstances by the use of the Mill-bank spring clip 18 which fits just above the welt of the boot at the instep. The Mill-bank clip is then secured to the foot member by the use of the elastic cord. The cord 15 is doubled, or any other number of turns taken about the foot member 13 with both hooks 16 thereof threaded through the Mill-bank clip 18. The extent of traction can be adjusted against the elastic of the cord 15, by varying the length of the splint leg member.

In a form of the invention which has been made, the rescue splint fits into the side pocket of a Mountain Mule tramper's pack which weighs approximately 1.1 k.g. complete.

Apart from its obvious advantages for rescue and military work, the rescue splint can be carried in vehicles and, in any circumstances where road or industrial accidents are likely.

After a few minutes instruction, the splint may be assembled and applied by lay personnel with safety and speed.

The splint and malleable ring is most desirable both in rescue work in applying the splint to different sized persons and as a safety feature which avoids the cutting off of circulation of blood to the leg in both first aid and in definitive treatment in hospitals.

We claim:

1. A splint comprising a foot member, a ring member, and a pair of leg members, said ring member having a malleable core and being discontinuous, positioning means positioning the pair of leg members on the ring member, said positioning means including, for each leg member, an apertured member passing over the core of the ring member and being positioned to prevent circumferential movement by an annular enlargement of the core on either side of said apertured member while permitting pivotal movement thereof on said core, said leg members being adjustable in length by providing telescopic tubular members into which rod members may telescope, compression clamps which are lockable to fix the rod members at a suitable relative position to the tubular members, said ring member being adjustable in diameter by being discontinuous and having a malleable core, a flexible resilient material covering said core, and a protective outer covering, the resilient material being divided over the discontinuity between the ends of the core, the divided portions being adapted to be fixed to each other with a fastening material, said positioning means in use restraining movement of said leg members around the periphery of said ring member but allowing pivoting relative to the plane of the ring member, the arrangement permitting adjustment of length of the leg members and adjustment of the obliquity of the ring member relative to the leg members to assist in adapting the splint to a patient.

2. A Thomas splint comprising a foot member, a ring member, and a pair of leg members, each leg member having opposite ends and being adjustable in length and engageable at one of the ends with said foot member, said ring member including a split malleable core having its free ends spaced apart to provide a gap therebetween for enabling the ring member to be passed transversely over a patient's limb and then adjusted to the required shape to suit the patient, means for positioning the other ends of said leg members on said ring members, said positioning means being defined by an apertured member for each leg member, each apertured member passing over the core of the ring member and a bulbous enlargement on the core on both sides of each apertured member restraining movement of said leg members around the periphery of said ring member but allowing pivotal movement of said leg members on said core, a flexible resilient tube covering said core and at least part of the apertured members, said tube having extensions which protrude beyond the free ends of said core, each extension having a flat surface, with said flat surfaces facing each other, and inter-engaging material on said flat surfaces so that after placing on a patient and adjusting the core as to position and length, the extensions can be secured to each other by the flat surfaces for providing a continuous protected covering over the core and the gap between the free ends of the core.

* * * * *